(12) United States Patent
Lou

(10) Patent No.: US 10,124,188 B2  
(45) Date of Patent: Nov. 13, 2018

(54) MAGNETIC MOXIBUSTION NECK PROTECTING APPARATUS

(71) Applicant: Zhongping Lou, Hangzhou (CN)

(72) Inventor: Zhongping Lou, Hangzhou (CN)

( * ) Notice: Subject to any disclaimer, the term of this patent is extended or adjusted under 35 U.S.C. 154(b) by 62 days.

(21) Appl. No.: 15/217,249

(22) Filed: Jul. 22, 2016

(65) Prior Publication Data

US 2017/0182331 A1    Jun. 29, 2017

(30) Foreign Application Priority Data

Dec. 28, 2015    (CN) .................... 2015 2 1113883 U

(51) Int. Cl.
| | |
|---|---|
| *A61N 2/00* | (2006.01) |
| *A61F 7/02* | (2006.01) |
| *A61F 5/055* | (2006.01) |
| *A61N 2/06* | (2006.01) |
| *A61F 7/00* | (2006.01) |

(52) U.S. Cl.
CPC ............. *A61N 2/002* (2013.01); *A61F 5/055* (2013.01); *A61F 7/02* (2013.01); *A61N 2/06* (2013.01); *A61F 2007/0011* (2013.01); *A61F 2007/0206* (2013.01)

(58) Field of Classification Search
CPC . A61N 2/002; A61F 5/055; A61F 7/02; A61F 2007/0011; A61F 2007/0206
See application file for complete search history.

(56) References Cited

U.S. PATENT DOCUMENTS

| 5,344,384 A * | 9/1994 | Ostrow .................. A61N 1/325 600/13 |
| 5,950,239 A * | 9/1999 | Lopez ...................... A41B 9/00 2/113 |
| 2009/0050657 A1* | 2/2009 | Woolery .................. A45F 3/14 224/183 |

* cited by examiner

*Primary Examiner* — Christine H Matthews  
*Assistant Examiner* — Joshua D Lannu  
(74) *Attorney, Agent, or Firm* — Leon E. Jew; Dahyee Law Group

(57) ABSTRACT

The present invention is a magnetic moxibustion neck protecting apparatus, including: a textile and multiple magnetic stripes fixed and distributed on the described textile; the multiple magnetic stripes are set based on the preset primary spacing; the described magnetic stripes include substrate and multiple magnets set on the stripes based on the preset secondary spacing; the described textile has a piece which is protruded outward from the center to form an arc and allow the apparatus to form fit around the neck. The magnetic moxibustion neck protecting apparatus provided by this utility model can conduct magnetotherapy with good efficacy.

5 Claims, 1 Drawing Sheet

MAGNETIC MOXIBUSTION NECK PROTECTING APPARATUS

REFERENCE TO RELATED APPLICATIONS

The present invention is related to the Chinese Patent Application No. 201521113883.3 filed on Dec. 28, 2015. The present invention claims the priority date of Chinese Patent Application No. 201521113883.3

FIELD OF THE INVENTION

The present invention generally relates to the field of magnetic therapy. More particularly, the invention relates to magnetic moxibustion technology and a type of magnetic moxibustion neck protecting apparatus

BACKGROUND OF THE INVENTION

In recent years, magnetotherapy has been developed rapidly due to its adaptability to a wide range of symptoms and includes the benefits of significant health effects, non-invasiveness, no physical pain, little side effects, safety, reliability, ease to learn and understand, inexpensiveness, and other advantages. It has now been a new type of treatment method that is widely promoted. Magnetotherapy is so-called therapy by magnetic field, which is a common name for treatment approaches of diseases by magnetic force or magnetic fields. Normally, the site that is going to be treated is placed in a dynamic magnetic field, in order to achieve the goal of promoting blood circulation, removing blood stasis, reducing swelling, relieving pain, diminishing inflammation, analgesia, etc. by impacting human tissues based on the magnetism produced by magnetic poles. As there are more and more people sitting in the office and facing the computer, driving and reading for a long time, plenty of problems in cervical spondylosis are brought about. Thus, a neck protecting apparatus, which can protect cervical vertebrae, relieving pain for cervical spondylosis and stiff neck, as well as protecting and keeping cervical vertebrae warm for healthy people, is urgently needed.

SUMMARY OF THE INVENTION

Accordingly, the present invention is a magnetic moxibustion neck protecting apparatus, including: a textile and multiple magnetic stripes fixed and distributed on the described textile; the multiple magnetic stripes are set based on the preset primary spacing; the described magnetic stripes include substrate and multiple magnets set on the stripes based on the preset secondary spacing; the described textile has a piece which is protruded outward from the center to help to form fit around the neck. The magnetic moxibustion neck protecting apparatus provided by this utility model can conduct magnetotherapy with good efficacy. Several different embodiments of the magnetic moxibustion neck protecting apparatus can be constructed. In one embodiment the described textile can be protruded outward from the center along with one end of the width direction. Alternatively, the described textile can also be protruded outward from the center to form an arc.

In another embodiment the distance of the described multiple magnetic stripes decreases gradually towards both sides symmetrically to the textile's center, as well as the number of magnets in the described multiple stripes. Another alternative embodiment includes the described magnetic stripes being set on the textile through sewing or adhesion. In addition, another alternative embodiment includes multiple grooves on the described textile, while the magnetic stripes are set into the grooves.

In yet another embodiment of the present invention, there are two connectors that can be mutually fastened on two ends of the textile to completely cover and protect the neck. The magnetic moxibustion neck protecting apparatus includes: a textile and multiple magnetic stripes fixed and distributed on the surface of the textile; the multiple magnetic stripes are set based on the preset primary spacing; the described magnetic stripes include substrate and multiple magnets sent on the substrate based on the preset secondary spacing; the textile has its central point protruding outward from center, in which case it can protect the cervical vertebrae without impact on beauty and mitigate pain for cervical spondylosis and a stiff neck, as well as protecting and keeping cervical vertebral warm for healthy people as well.

DETAILED DESCRIPTION OF THE INVENTION

Figure 1:
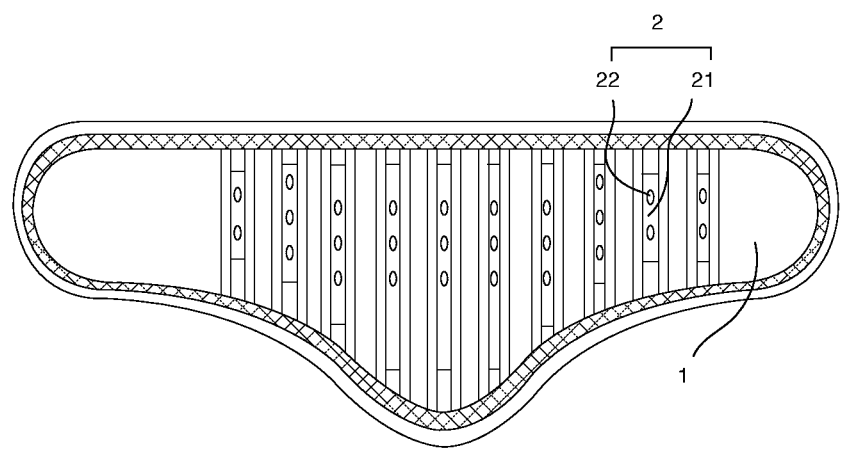
FIG. 1 is an illustration of the front view of the magnetic moxibustion neck protecting apparatus of the present invention.

While the present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

First Preferred Embodiment

FIG. 1 is an illustration of the structure of one embodiment of the magnetic moxibustion neck protecting apparatus as shown in FIG. 1, the magnetic moxibustion neck protecting apparatus includes: textile 1 and multiple magnetic stripes 2 set on the described textile; the described multiple magnetic stripes are set based on the preset primary spacing. The described magnetic stripes 2 include substrate 21 and multiple magnets 22 set on the described substrate 21 based on the preset secondary spacing. Further, the described textile 1 is protruded outward from the center. The preset primary spacing can have different distance values, as long as the magnetic field produced by magnetic stripes is relatively large. The substrate is set on the textile 1. In this embodiment, the textile 1 can be a knitted fabric. For example, if multiple magnets 22 are set on the substrate 21, and the substrate are then set on the textile, a type of magnetic moxibustion neck protecting apparatus is formed. In this embodiment, magnetic stripes 2 can be set on textile 1 through sewing or adhesion. A detailed fixation approach can be chosen based on practical application, and there is no restriction in this embodiment. In this embodiment, the multiple magnets 22 are magnetically permeable material. In order to prevent the disturbance of substrate on multiple magnetic stripes, material of the substrate is not magnetically permeable, it can be a flexible substrate as well.

As shown in FIG. 1, the described textile 1 is protruded outward along with one end of the width direction. As shown in FIG. 1, the extending direction of the magnetic stripes is parallel to the longitudinal direction of textile 1. In order to treat and protect the cervical vertebrae, textile 1 is protruded outward from the center along with one end of the width direction, in order to better cover cervical vertebrae. Furthermore, heat treatment can be conducted on the substrate in other embodiments in order to obtain a hot magnetic moxibustion neck protecting apparatus combined with high temperature and strong magnetic forces. This can conduct fomentation and magnetotherapy on users to achieve health care, and the temperature for fomentation can be automatically controlled.

The magnetic moxibustion neck protecting apparatus includes: a textile and multiple magnetic stripes fixed and distributed on the described textile. The multiple magnetic stripes are set based on the preset primary spacing; the described magnetic stripes include substrate and multiple magnets set on the substrate based on the preset primary. The center of the textile protrudes outward from the center along with one end of the width direction, in which case it can protect the cervical vertebrae to relieve pain of cervical spondylosis and stiff neck without impact on beauty. It also can protect and keep the cervical vertebrae warm for healthy people.

Figure 2:
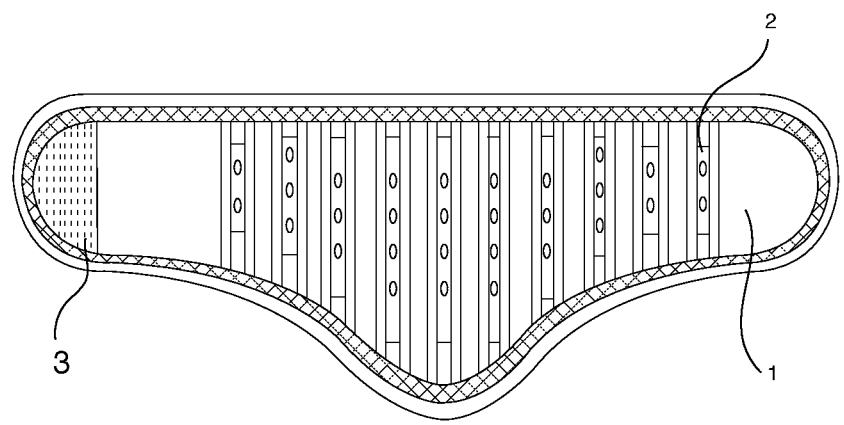
FIG. 2 is an illustration of the front view including detailed features of the magnetic moxibustion neck protecting apparatus of the present invention.

FIG. 2 is an illustration of the structural figure of another embodiment of the magnetic moxibustion neck protecting apparatus. Based on the above embodiments, the center of the textile then protrudes outward from the center and forms an area as shown in FIG. 2. One side of the described textile is protruded outward from the center to form an arc for the purpose of enhancing cosmetic appearance, while one of the multiple stripes 2 is set at the center of the textile 1. As shown in FIG. 2, the other magnetic stripes are set are set symmetrically to the one at the center of textile 1. The magnetic stripe at the center of the textile 1 is the longest as shown in FIG. 2. Furthermore, the length of the multiple magnetic stripes 2 decreases gradually towards both sides symmetrically to the center of the textile 1, as well as the number of magnets 22 in magnetic stripes 2. As shown in FIG. 2, the length of the magnetic stripe at the center of the textile 1 is 75 mm with 5 magnets. The length of the other magnetic stripes gradually decreases towards both sides to 70 mm, 55 mm, 40 mm, and 30 mm with 4, 3, 2, and 1 magnet respectively. The length of textile in FIG. 2 is 475 mm, and its largest width is 110 mm.

Furthermore, the described preset primary spacing can be set as uniform as well. In this embodiment, the preset primary is 20-40 mm, and the primary spacing as shown in FIG. 2 is 30 mm. In addition, in this embodiment, the preset distance between multiple magnets is 10-30 mm. Moreover, relatively large magnetic field strength is guaranteed by setting the multiple magnets on the substrate based on preset spacing of 10-30 mm. When the magnetic field acts on the human body, it has stronger penetrating power. Magnetic lines can penetrate into the skin to enhance the effect of the magnetic field on the human body to improve the body's microcirculation. Furthermore, by setting multiple magnets on the substrate based on different preset spacing, different magnetic moxibustion neck protecting apparatus' can be obtained to satisfy different user's needs. Users can also choose to set multiple magnets on different types of textiles based on their own needs while also being able to adjust the position of the magnetic stripes on the textile.

In addition, based on the above embodiments, multiple magnetics can be arranged based on a unipolar direction when they are set on the substrate in this embodiment. They can also be arranged based on a bipolar direction in that, a unipolar directional arrangement means that N pole or S pole of the multiple magnets has the same direction, while bipolar directional arrangement means their N pole or S pole has different directions. Furthermore, multiple grooves can be set on the textile 1, and the described magnetic stripes can be set into the grooves. Specifically, one magnetic stripe can be set in one groove correspondingly. Yet in an alternative arrangement, multiple magnetic stripes can also be set on the textile through multiple connectors that are set in grooves, and the magnetic stripes can be set in the grooves through sewing or adhesion. As shown in FIG. 2, there are connectors 3 that can be mutually fastened on two ends of the textile 1.

Although one or more embodiments of the newly improved invention have been described in detail, one of ordinary skill in the art will appreciate the modifications to the material selection and utility functions of the neck protecting apparatus along with the new magnetic stripe layout of the magnetic moxibustion neck protecting apparatus. In particular, by using the layout of the multiple magnetic stripes starting with the longest stripe according designed to run down the center of the user's neck, a desirable assembly and more effective footprint is created to enhance magnetic therapy for humans. It is acknowledged that obvious modifications will ensue to a person skilled in the art. The claims which follow will set out the full scope of the claims.

The invention claimed is:

1. An apparatus configured to be applied around a user's neck to protect the user's neck and to perform magnetic moxibustion therapy comprising:
    a textile having a top, bottom, left and right sides, multiple magnetic stripes, a substrate, and multiple magnets inside the multiple magnetic stripes;
    wherein the multiple magnetic stripes are affixed and distributed on the textiles;
    wherein the multiple magnetic stripes and multiple magnets are set on a preset spacing on the textile;
    wherein the textile protrudes from a center to form an arc;
    wherein one of the multiple magnetic stripes is affixed at the center of the textile and perpendicular to the textile's top side, and other multiple magnetic stripes are placed parallel to the one magnetic stripe at the center while other multiple magnetic stripes decrease gradually in length towards the textile's left side and right side symmetrically according to the one magnetic stripe at the center; and
    wherein the magnets in the multiple magnetic strips decrease in number relative to the length of the multiple magnetic stripes.

2. The apparatus configured to be applied around a user's neck to protect the user's neck and to perform magnetic moxibustion therapy according to claim 1 wherein the preset spacing on the textile is between 20 mm and 40 mm.

3. The apparatus configured to be applied around a user's neck to protect the user's neck and to perform magnetic moxibustion therapy according to claim 1 wherein the multiple magnetic stripes can be fixed on the textile by sewing.

4. The apparatus configured to be applied around a user's neck to protect the user's neck and to perform magnetic moxibustion therapy according to claim 1 wherein the textile has multiple grooves and the multiple magnetic stripes are set into the grooves to form sleeves.

5. The apparatus configured to be applied around a user's neck to protect the user's neck and to perform magnetic moxibustion therapy according to claim 1, further comprising two connectors that can be mutually fastened on two ends of the textile to completely cover and protect the user's neck.

\* \* \* \* \*